United States Patent [19]

Park

[11] Patent Number: 5,124,461
[45] Date of Patent: Jun. 23, 1992

[54] PROCESS FOR THE PRODUCTION OF TRIMELLITIC ANHYDRIDE WITH IMPROVED COLOR

[75] Inventor: Chang-Man Park, Naperville, Ill.

[73] Assignee: Amoco Corporation, Chicago, Ill.

[21] Appl. No.: 740,606

[22] Filed: Aug. 5, 1991

Related U.S. Application Data

[63] Continuation of Ser. No. 565,508, Aug. 9, 1990, abandoned, which is a continuation-in-part of Ser. No. 396,852, Aug. 22, 1989, abandoned.

[51] Int. Cl.$^5$ ............................................. C07D 307/89
[52] U.S. Cl. .................................................. 549/245
[58] Field of Search ........................................ 549/245

[56] References Cited

FOREIGN PATENT DOCUMENTS 1948374  4/1970  Fed. Rep. of Germany .

Primary Examiner—Mukund J. Shah
Assistant Examiner—Philip I. Datlow
Attorney, Agent, or Firm—Gunar J. Blumberg; William H. Magidson; Frank J. Sroka

[57] ABSTRACT

A process for the production of trimellitic anhydride with improved color is disclosed. The process comprises heat treating trimellitic anhydride in the presence of oxides of boron or hydrated oxides of boron followed by fractionation. Trimellitic anhydride is used in the manufacture of polyesters and polyamide-imides.

6 Claims, No Drawings

PROCESS FOR THE PRODUCTION OF TRIMELLITIC ANHYDRIDE WITH IMPROVED COLOR

This is a continuation of application Ser. No. 07/565,508, filed Aug. 9, 1990, which is a continuation-in-part of U.S. Ser. No. 396,852, filed Aug. 22, 1989, both now abandoned.

BACKGROUND OF THE INVENTION

1. Field of the Invention

This invention relates to trimellitic acid anhydride (TMA) and more particularly is concerned with an improved process for the preparation of trimellitic anhydride relatively free from color bodies to obtain a relatively color-less trimellitic anhydride. The invention has particular applicability when the trimellitic anhydride has been produced by a series of reactions and procedures which result in a darkly-colored product, characteristically of a dark brown color.

2. Background

Trimellitic acid (TMLA), the 1,2,4 benzene tricarboxylic acid, is useful as an intermediate in the production of quality plasticizers and polyester resins. For these applications, in which trimellitic acid is esterified with a monohydric or a polyhydric alcohol, the evolution of water as an esterification by-product together with the attendant difficulty of eliminating water from esterification reaction mixtures favors the desirability of employing trimellitic acid as the anhydride rather than as the acid. Resins and plasticizers may further require a trimellitic anhydride which is relatively free from color bodies and also free from the heavy metals employed as catalysts for the air oxidation of aliphatic-substituted benzenes to produce trimellitic acid. A Delta E color of below 2 is often specified for trimellitic anhydride used in white or transparent resins, and a metal content of less than about 50 p.p.m. (parts per million) is desirable to achieve good color and oxidation stability. While the more commonly employed maleic and phthalic acid anhydrides are readily prepared by thermal dehydration of the corresponding acids, and the anhydrides are easily purified by atmospheric pressure sublimation, trimellitic anhydride cannot be processed in this manner. Firstly, the acid requires temperatures in excess of 200° C. for thermal dehydration to take place, and even at these temperatures dehydration is not complete. Secondly, trimellitic anhydride is essentially non-volatile and must be distilled at temperatures above 250° C. under vacuums on the order of 10–60 mm mercury absolute to prevent color degradation. Also, to increase the ordinarily slow rate of dehydration, it has previously been proposed to employ chemical dehydrating agents such as acetic anhydride, sulfuric acid, phosphorus pentoxide, or the like to dehydrate the last traces of trimellitic acid before distilling the anhydride. These chemical dehydrating agents are costly to recover and regenerate, and consequently impose an expensive operating burden on existing processes for the purification of trimellitic anhydride. Furthermore, their use in some cases results in the substitution of one impurity for another.

Typically, the product resulting from any or all of these procedures can be of a color which is undesirable for product to be used in many applications. It is therefore essential to obtain a product relatively free of color bodies in order to obtain a relatively colorless trimellitic anhydride.

The presence of color bodies is frequently measured by optical scanning equipment, such as available from the Milton Roy Company, Ivyland, Pa. A Milton Roy Color Scan II colorimeter can be used to measure the Delta E color level of trimellitic anhydride. A Delta E color of 1.5 or below is a preferred color level.

Accordingly, an object of the present invention is to provide an improved process for preparing trimellitic anhydride relatively free from color bodies having a Delta E color below 1.5 and a metal content below 50 p.p.m. Other and more particular objects will become apparent as the description of this invention is set forth in detail hereinafter.

SUMMARY OF THE INVENTION

A process is disclosed to prepare trimellitic anhydride having Delta E color below 1.5 by heat treating trimellitic anhydride having a Delta E color greater than 1.5 in the presence of oxides or hydrated oxides of boron followed by fractionation.

PRIOR ART

In the prior art German Patent Publication 19 48 374, trimellitic acid is treated with boric acid. In our improved process, trimellitic anhydride is heated to a temperature of about 200° to about 300° C. in the presence of oxides and hydrated oxides of boron at a decreased pressure and distilled under further decreased pressure at a temperature of about 200° to about 275° C.

DETAILED DESCRIPTION OF THE INVENTION

In an embodiment of the instant invention, about 0.1 to about 1.0 weight percent of an oxide or hydrated oxide of boron, e.g., boric acid, is added to TMA and heated to a temperature of about 200° to about 300° C. for a period of about 30 to about 480 minutes, preferably about 60 to about 240 minutes in an inert gas atmosphere with stirring. After this preliminary heat soak, the trimellitic anhydride is fractionated under a decreased pressure of about 1 to about 25 mm Hg, preferably about 5 to about 15 mm Hg.

Crude trimellitic acid may be prepared by the oxidation of various 1,2,4-aliphatic-substituted benzenes by way of several known routes. Chemical oxidizing agents such as nitric acid, chromic acid, potassium permanganate and the like can oxidize a tri-alkylbenzene such as pseudocumene directly to trimellitic acid. Rather than use chemical oxidizing agents, molecular or gaseous oxygen may be employed to effect a liquid phase oxidation of an aliphatic-substituted benzene in the presence of a heavy metal oxidation catalyst such as cobalt or manganese. In this manner, 1,2,4-trimethyl benzene is oxidized to trimellitic acid. Another process involving molecular-oxygen oxidation is the heavy-metal-catalyzed liquid phase oxidation of pseudocumene by repeatedly oxidizing one methyl radical to a carboxyl group, esterifying that carboxyl group with a lower alkanol, and oxidizing another methyl radical on the intermediate to another carboxyl group, followed by hydrolysis of the dialkanol ester of trimellitic acid to trimellitic acid. A more direct preparation is the one step oxidation of a trialkylbenzene such as pseudocumene with molecular oxygen in an inert liquid medium at about 150°–250° C. employing a catalyst comprising, in conjoint presence, a heavy metal oxidation catalyst and bromine. Suitable metal catalysts are selected from metals having atomic numbers of 13, 21-32, 39-51, 57-84 all inclusive, and the actinide earths, and may be added either in elemental form or as a soluble compound such as cobalt chloride, iron acetate, ammonium chromate, manganese acetyl acetonate, or the like. Likewise, bromine may be added as elemental bromine, HBr, sodium bromide, nickel bromide, benzyl bromide, etc. Trimellitic acid yields from the air oxidation of pseudocumene in the presence of a heavy metal oxidation catalyst and bromine are in excess of 160 weight percent. Trimellitic acid can then be dehydrated to trimellitic anhydride.

However, when trimellitic anhydride is prepared from trimellitic acid, the resulting trimellitic anhydride, as a result of a series of reactions and procedures, can be of a product of some color and characteristically of a color level greater than a Delta E of 1.5 and dark brown in color.

It has now been discovered that trimellitic anhydride having Delta E color below 1.5 can readily be obtained by heat treating trimellitic anhydride having a Delta E color greater than 1.5 in the presence of oxides or hydrated oxides of boron followed by fractionation. A trimellitic anhydride of a color level within a Delta E of from about 0.71 to about 1.50 can also be treated by the process of the instant invention to prepare a trimellitic anhydride with a color level less than a Delta E of 0.71.

It has been found that a heat soak of trimellitic anhydride having a color greater than a Delta E of 1.5 is necessary for the instant invented process at a temperature within the range of from about 200° C. to about 300° C., preferably within the range of from about 230° C. to about 275° C., more preferably at a temperature of from 250° C. to 275° C., in the presence of an oxide or hydrated oxide of boron for a period of from about 60 minutes to about 480 minutes, preferably from about 60 minutes to about 240 minutes, more preferably for a period less than 120 minutes under an inert gas atmosphere. The heat soak is then followed by fractionation of the trimellitic anhydride under reduced pressure of less than about 60 mm Hg, preferably from about 1 to 25 mm Hg, more preferably from about 5 to about 15 mm Hg. Fractionation at pressures greater than 60 mm Hg can result in color degradation of the trimellitic anhydride.

The level of the oxide or the hydrated oxide of boron present in the heat soak procedure is critical in reducing the Delta E color. Although results can be obtained in reducing the Delta E color by a concentration of a boron oxide or hydrated oxide of boron as low as 0.1 wt. % relative to weight of trimellitic anhydride present, a concentration of at least 0.50 wt. % of the boron compound, in combination with a heat soak temperature of about 250° C. to about 275° C., can reduce the Delta E color to a level below 1.0, a level desirable for commercial applications.

The analytical procedure for determining the Delta E color level of trimellitic anhydride using Milton Roy Color Scan II can require several pieces of equipment.

TMA DELTA E Procedure on the Milton Roy Color Scan II

A typical equipment setup in current use for the DELTA E procedure consists of a Milton Roy Color Scan II colorimeter, an Adds 1010 video monitor, and an IBM Proprinter. The printer is connected in a fashion to simply print out whatever appears on the Adds 1010 video monitor screen.

I. Start-Up Procedure

A. Initialization

During normal operation the instrument is turned on at all times (e.g., both when in use and when not in use). In this state only the LED indicator for the "INITIALIZE" button will be on. The lamp should be turned off when the unit is not being used in order to prolong lamp life. In the event of a power outage/surge the Color Scan needs to be reinitialized. This is accomplished by simply pressing the "INITIALIZE" button (Blue) on the instrument control panel. This procedure will clear all hardware and software flags and will set the microprocessor in default status. This key can be pressed whenever the operator wishes to abort all action and restart. The factory default settings are listed below along with the values used in the TMA DELTA E measurement.

| Default | TMA Setting |
| --- | --- |
| DF = 1 | DF = 2 |
| IL = 7 | IL = 1 |
| OB = 0 | OB = 0 |
| PR = 1 | PR = 0 |
| PT = 1 | PT = 3 |
| AV = 1 | AV = 1 |
| CR = 1 | CR = 1 |
| SC = 1 | SC = 1 |
| PF = 0 | PF = 1 |
| RF = 0 | RF = 0 |
| WS = 380 | WS = 380 |
| WE = 700 | WE = 700 |
| WI = 10 | WI = 10 |
| CLOW = 70 | CLOW = 40 |
| CHIGH = 130 | CHIGH = 150 |

To determine whether the variables are set to their proper values enter the command "CF" from the Adds Video Monitor. The variables will then be displayed on the screen and will be printed on the printer. To change a value simply type in the variable and the new value (e.g. type in DF=2 and press the return key).

B. Lamp

The lamp should be turned on for at least thirty minutes prior to calibration or performing measurements. To turn on the lamp, either press the "LAMP" (Green) button on the instrument control panel or enter the command "LAMPON" from the Adds Video Monitor. At the end of either command the LED indicator for the lamp on the instrument control panel will be on, indicating the command was carried out. After completing the measurements, the lamp should be turned off by either pressing the "LAMP" (green) button on the instrument control panel or entering the command "LAMPOFF" from the Adds Video Monitor. The LED indicator for the lamp will be off.

C. Calibration

The calibration procedure should be performed every day after the lamp has warmed up. This assures that calculations will be made against absolute values for reflectance measurements and 100% beam balance for transmittance measurements. The reference tile marked "R" and the Sample Tile marked "S" should be placed in their respective ports. Make sure all parameters are correctly set as described in Section A above.

Open the transmission compartment and make sure that both the SPIN/SPEX slide and the small Area View Lever are in the "up" position. To calibrate the instrument simply press either the "CALIBRATE" (Yellow) button on the instrument control panel or enter the command "CA" from the Adds Video Monitor. During the calibration process, the LED indicator for the "CALIBRATE" button will be on. Upon completion of the command an asterisk will appear on the Adds Video Monitor screen and the LED indicator for the "CALIBRATE" button will be off.

In general, the instrument must be recalibrated any time the beginning wavelength (WS), the ending wavelength (WE) or the wavelength increment (WI) is changed. If not, a scan format error will be issued. Additionally, the instrument should be recalibrated when the calibration type (SC), the SPIN/SPEX Slide, or the optics are changed.

Patent application U.S. Ser. No. 396,852 filed Aug. 22, 1989, now abandoned, is specifically incorporated by reference herein.

In summary, the instant invented process comprises a procedure for the production of trimellitic anhydride with improved color level of said trimellitic anhydride is less than a Delta E of 1.5, the process comprising heat treating trimellitic anhydride having a color level at least or greater than a Delta E of 1.5 in the presence of oxides of boron or hydrated oxides of boron at a least 0.1 wt. % of the weight of said trimellitic anhydride, followed by fractionation of said trimellitic anhydride at a temperature within the range of from about 200° C. to about 275° C. and a pressure of less than 60 mm Hg, preferably from about 1 mm Hg to about 25 mm Hg. Preferably the heat treating is conducted at a temperature within the range of from about 230° C. to about 275° C. More preferably, the heat treating is conducted at a temperature within the range of from about 250° C. to about 275° C., a treat level of said oxides of boron or hydrated oxides of boron of from about 0.25 wt. % to about 0.75 wt. % of said trimellitic anhydride. Preferably the oxide of boron is boric acid. The instant invented process also comprises heat treating at a temperature within the range of from about 200° C. to about 300° C. trimellitic anhydride at a color level within the range of a Delta E of from about 0.71 to about 1.50 to prepare a trimellitic anhydride with a color level less than a Delta E of 0.71.

To further illustrate various embodiments of the present invention several examples are provided hereinafter, it being understood that they are illustrative only.

EXAMPLE 1

Charged 250 grams of TMA to a 500 ml feed pot along with 1.25 grams of boric acid. The TMA was a dark brown color with a Delta E of 95.6. Treat level was 0.50 wt. %. The material was heated to 250° C. and held at the temperature for four (4) hours while magnetically stirred. The material was cooled to 180° C. while the fractionator heater was turned on to stabilize the temperatures to the desired level. A vacuum pump was then turned on and maintained at around 5 mm Hg. The feed pot temperature was then raised again to an appropriate fractionation temperature. The product TMA of a nearly water white color was collected as an overhead condensate. The DELTA E color of the TMA product was 0.68 compared to the TMA color of 2.5 to 3.0 obtained from a fractionation without the boron treatment.

EXAMPLE 2

Charged 250 grams of TMA to a feed pot along with 1.25 grams of boric acid. Treat level of boric acid was 0.50 wt. %. The TMA was a dark brown color with a Delta E of 95.6. The material was heated to 275° C. and held at the temperature for 2 hours. Subsequently, the material was fractionated following the similar procedure as described in Example 1. The resulting product of a nearly water white color had a DELTA E color of 0.71.

EXAMPLE 3

Charged 400 grams of trimellitic acid to a feed pot along with 2.00 grams of boric acid. The trimellitic acid was a light brown color with a Delta E of 54.5. Treat level of boric acid was 0.55 wt. %, based on the TMA value. The material was heated to 235° C. over the span of 3.5 hours, dehydrating TMLA to TMA. Subsequently, the material was fractionated following the similar procedure as described in Example 1. The DELTA E color of the TMA product was 1.12 and color was slightly offwhite. This shows that the addition of boric acid to TMLA is not as effective as the addition of boric acid to TMA.

EXAMPLE 4

Charged 250 grams of TMA to a 500 ml feed pot. The TMA was a dark brown color with a Delta E of 95.6. No boric acid was added. The material was heated to 275° C. and held for 8 hours. After the heat soak, the material was fractionated following the similar procedure as described in Example 1. The DELTA E of the product TMA was 2.67, showing that the heat soak alone without boric acid does not improve the product color to a Delta E of less than 1.5. EGC analysis of the product showed a substantial increase in isophthalic acid, terephthalic acid, and orthophthalic acid, indicating that a prolonged heat treatment is undesirable for the product purity.

EXAMPLE 5

Charged 250 grams of TMA to a feed pot. The TMA was a dark brown color with a Delta E of 95.6. Fractionation was started right away without any heat treatment and without any additives. The resulting product had a DELTA E color of 2.69. As stated in Example 1 above, this level of color results if heat treatment or additives such as boron oxides are eliminated.

EXAMPLE 6

In the procedure of Example 1, 250 grams of TMA were charged to a 500 ml feed pot along with 0.625 grams of boric acid, a treat level of 0.25 wt. % of the TMA. The color of the TMA was dark brown and Delta E was 95.6. The material was heated to 275° C. for a period of 2 hours. Subsequently, the material was fractionated following the same procedure as described in Example 1. The resulting product had a Delta E color of 1.08.

The above example illustrates that to obtain a Delta E level below 1.0, a concentration of about a 0.25 wt. % level of a boron oxide or hydrated oxide of boron to the TMA present is not sufficient to obtain a Delta E below 1.0 despite a temperature of 275° C. and a heat soak of 2 hours.

EXAMPLE 7

The procedure of Example 6 was repeated except that the boric acid concentration was increased to a treat level of 0.50 wt. % of the TMA present by adding 1.25 grams of boric acid. Heat soak period was 2 hours, and heat soak temperature was 275° C. The resulting product had a Delta E of 0.71.

The above example illustrates that at a heat soak temperature of 275° C., a heat soak period of 3 hours, and a boric acid treat level of 0.50 wt. % of TMA present, the Delta E level of 95.6 TMA, a dark brown color can be reduced to a Delta E below 1.0 to a level of 0.71.

That which is claimed is:

1. A process for the production of trimellitic anhydride with a color level less than a Delta E of about 1.0, the process comprising heat treating at a temperature within the range of from about 250° C. to about 275° C., trimellitic anhydride of a color level greater than a Delta E of about 1.0 in the presence of oxides of boron or hydrated oxides of boron at a treat level of at least 0.5 wt % of the weight of trimellitic anhydride followed by fractionation at a temperature of about 200° C. to about 275° C. and a pressure less than about 60 mm Hg.

2. The process of claim 1 wherein said pressure is within the range of from about 1 to 25 mm Hg.

3. The process of claim 1 wherein the heat treating is conducted at a temperature of about 250° C. to about 275° C. for a period of at least 60 minutes.

4. The process of claim 1 wherein said heat treating is conducted at a temperature within the range of from about 250° C. to about 275° C., treat level of said oxides of boron or hydrated oxides of boron is from 0.50 wt. % to 0.75 wt. % of said trimellitic anhydride.

5. The process of claim 1 wherein the heat treating is conducted in the presence of boric acid.

6. The process of claim 1 wherein said process comprises heat treating at a temperature within the range from about 250° C. to about 275° C. trimellitic anhydride to prepare a trimellitic anhydride with a color level less than a Delta E of 0.71.

* * * * *

UNITED STATES PATENT AND TRADEMARK OFFICE
CERTIFICATE OF CORRECTION

PATENT NO. : 5,124,461
DATED : June 23, 1992
INVENTOR(S) : Chang-Man Park

It is certified that error appears in the above-indentified patent and that said Letters Patent is hereby corrected as shown below:

| Column | Line |   |
|--------|------|---|
| 5 | 29 | "of boron at a least 0.1 wt.%" should read --of boron at a treat level of at least 0.1 wt.%-- |

Signed and Sealed this

Fourteenth Day of September, 1993

Attest:

BRUCE LEHMAN

*Attesting Officer*  *Commissioner of Patents and Trademarks*